United States Patent
Carpenter et al.

(10) Patent No.: US 10,293,180 B2
(45) Date of Patent: *May 21, 2019

(54) MULTI-OBJECTIVE RADIATION THERAPY SELECTION SYSTEM AND METHOD

(71) Applicant: Siris Medical, Inc., Redwood City, CA (US)

(72) Inventors: Colin Carpenter, San Carlos, CA (US); Ran Davidi, Sunnyvale, CA (US); Nicholas J. Mourlas, Mountain View, CA (US); Todd F. Atwood, Menlo Park, CA (US)

(73) Assignee: Siris Medical, Inc., Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/885,691

(22) Filed: Jan. 31, 2018

(65) Prior Publication Data

US 2018/0221684 A1 Aug. 9, 2018

Related U.S. Application Data

(63) Continuation of application No. 14/310,925, filed on Jun. 20, 2014, now Pat. No. 9,925,391.
(Continued)

(51) Int. Cl.
*A61N 5/10* (2006.01)
*G06F 19/00* (2018.01)
(Continued)

(52) U.S. Cl.
CPC ....... *A61N 5/1031* (2013.01); *G06F 19/3481* (2013.01); *G16H 10/60* (2018.01);
(Continued)

(58) Field of Classification Search
None
See application file for complete search history.

(56) References Cited

U.S. PATENT DOCUMENTS

| 5,511,549 | A | 4/1996 | Legg et al. |
| 6,038,283 | A | 3/2000 | Carol et al. |

(Continued)

FOREIGN PATENT DOCUMENTS

| WO | WO 2008016795 | 2/2008 |
| WO | WO 2012/080906 | 6/2012 |
| WO | WO 2013/049845 | 4/2013 |

OTHER PUBLICATIONS

D'Souza, Warren D. et al., "A nested partitions framework for beam angle optimization in intensity-modulated radiation therapy, Physics in Medicine and Biology", vol. 53, 2008, pp. 3293-3307.
(Continued)

*Primary Examiner* — Hoon K Song
(74) *Attorney, Agent, or Firm* — Fenwick & West LLP

(57) ABSTRACT

A system for facilitating creation of a patient treatment plan includes components configured to receive at least one feature associated with patient data and search a database of previously planned radiation treatments to identify one or more matching plans from the database based on the at least one feature. Parameters corresponding to the identified matching treatment plans may be used to facilitate creation of the patient treatment plan.

21 Claims, 3 Drawing Sheets

Related U.S. Application Data

(60) Provisional application No. 61/837,754, filed on Jun. 21, 2013, provisional application No. 61/877,291, filed on Sep. 13, 2013.

(51) Int. Cl.
  *G16H 10/60* (2018.01)
  *G16H 50/70* (2018.01)
  *G16H 20/40* (2018.01)

(52) U.S. Cl.
  CPC .............. *G16H 20/40* (2018.01); *G16H 50/70* (2018.01); *A61N 5/1039* (2013.01); *A61N 2005/1041* (2013.01)

(56) References Cited

U.S. PATENT DOCUMENTS

| | | |
|---|---|---|
| 6,327,490 B1 | 12/2001 | Spetz |
| 6,560,311 B1 | 5/2003 | Shepard et al. |
| 6,719,683 B2 | 4/2004 | Frohlich |
| 7,046,762 B2 | 5/2006 | Lee et al. |
| 7,206,377 B2 | 4/2007 | Svatos |
| 7,593,505 B2 | 9/2009 | Saracen et al. |
| 7,611,452 B2 | 11/2009 | Allison et al. |
| 7,820,989 B2 | 10/2010 | Sommer |
| 7,835,500 B2 | 11/2010 | Fu et al. |
| 7,876,882 B2 | 1/2011 | Meyer et al. |
| 8,121,252 B2 | 2/2012 | Nord et al. |
| 8,144,833 B2 | 3/2012 | Breedveld |
| 8,199,990 B2 | 6/2012 | Foshee et al. |
| 8,222,616 B2 | 7/2012 | Lu et al. |
| 8,232,535 B2 | 7/2012 | Olivera et al. |
| 8,346,354 B2 | 1/2013 | Hyde et al. |
| 8,363,784 B2 | 1/2013 | Soberting et al. |
| 8,688,618 B2 | 4/2014 | McNutt et al. |
| 9,925,391 B2 * | 3/2018 | Carpenter ........... G06F 19/3481 |
| 2002/0080915 A1 | 6/2002 | Frohlich |
| 2004/0071261 A1 | 4/2004 | Earl et al. |
| 2006/0173663 A1 | 8/2006 | Langheier et al. |
| 2008/0310590 A1 | 12/2008 | Meyer et al. |
| 2010/0054411 A1 | 3/2010 | Nord et al. |
| 2011/0106749 A1 | 5/2011 | Krishnan et al. |
| 2011/0124976 A1 | 5/2011 | Sabczynski et al. |
| 2011/0153547 A1* | 6/2011 | McNutt ............... G06F 19/3481 706/54 |
| 2011/0301977 A1 | 12/2011 | Belcher et al. |
| 2012/0059252 A1 | 3/2012 | Li et al. |
| 2012/0136194 A1 | 5/2012 | Zhang et al. |
| 2012/0310615 A1 | 12/2012 | Moore et al. |
| 2013/0072742 A1 | 3/2013 | Nord et al. |
| 2013/0272593 A1 | 10/2013 | Lee et al. |
| 2014/0205167 A1 | 7/2014 | Kleiner |
| 2014/0378736 A1 | 12/2014 | Fox et al. |

OTHER PUBLICATIONS

Gautier, Q. et al., "Development of a GPU Research Platform for Automatic Treatment Planning and Adaptive Radiotherapy RePlanning", presented at the AAPM 55th Annual Meeting & Exhibition, Meeting Program, Aug. 4-8, 2013, Indianapolis, Indiana, 1 page.

Zhang, Hao H. et al., "A two-stage sequential linear programming approach to IMRT dose optimization", Phys Med Biol., Feb. 7, 2010, vol. 55, No. 3, pp. 883-902.

Zhang, Hao H. et al., "Modeling Plan-Related Clinical Complications Using Machine Learning Tools in a Multi-Plan IMRT Framework", Int J Radiat Oncol Biol Phys. Aug. 1, 2009, vol. 74, No. 5, pp. 1617-1626.

International Search Report and Written Opinion issued in PCT/US2014/043474, dated Oct. 23, 2014, 11 pages.

European Extended Search Report, European Application No. 14813453.9, dated Dec. 12, 2016, 8 pages.

United States Office Action, U.S. Appl. No. 14/310,925, dated Jul. 6, 2017, 11 pages.

United States Office Action, U.S. Appl. No. 14/310,925, dated Jun. 27, 2016, 13 pages.

* cited by examiner

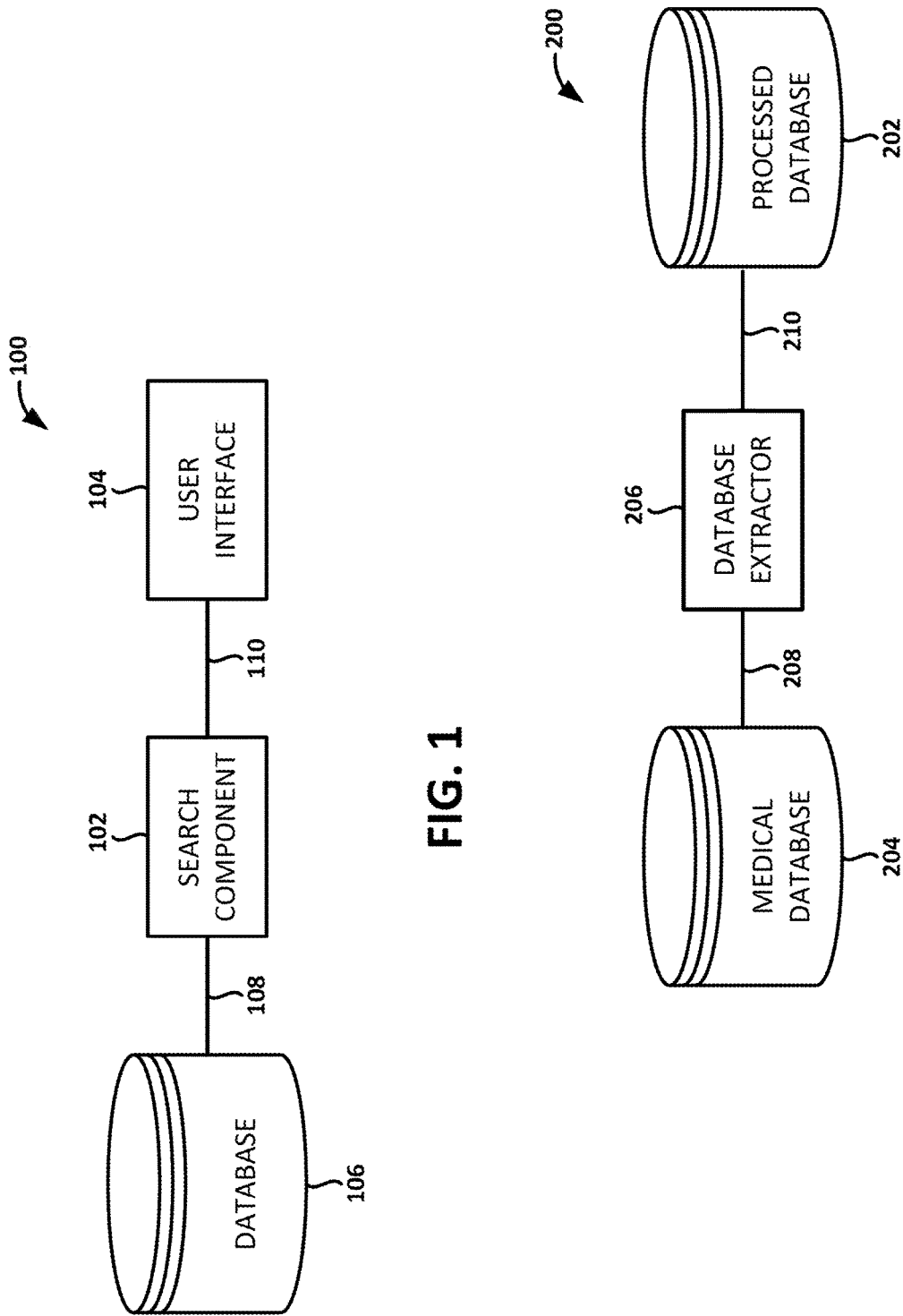

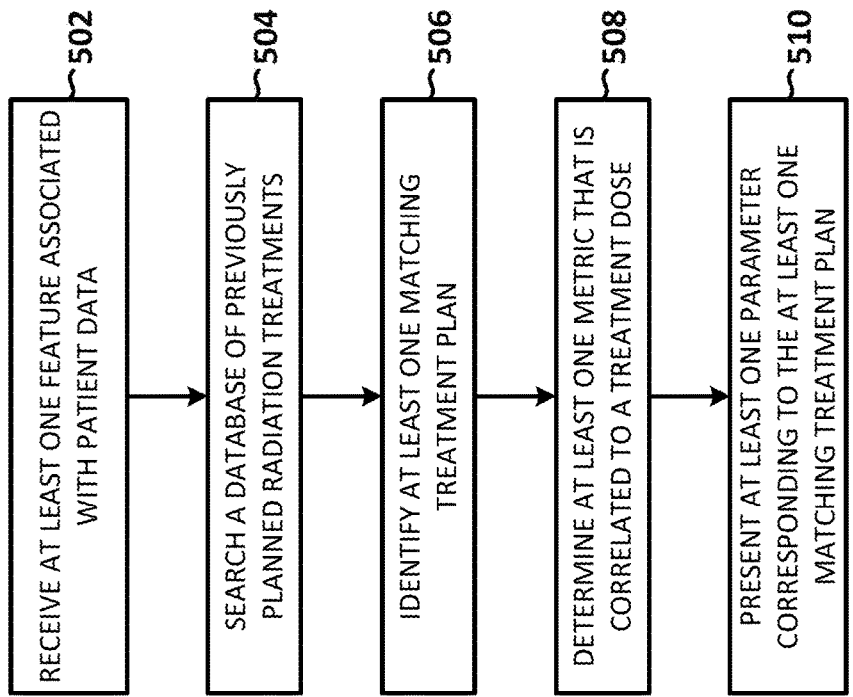
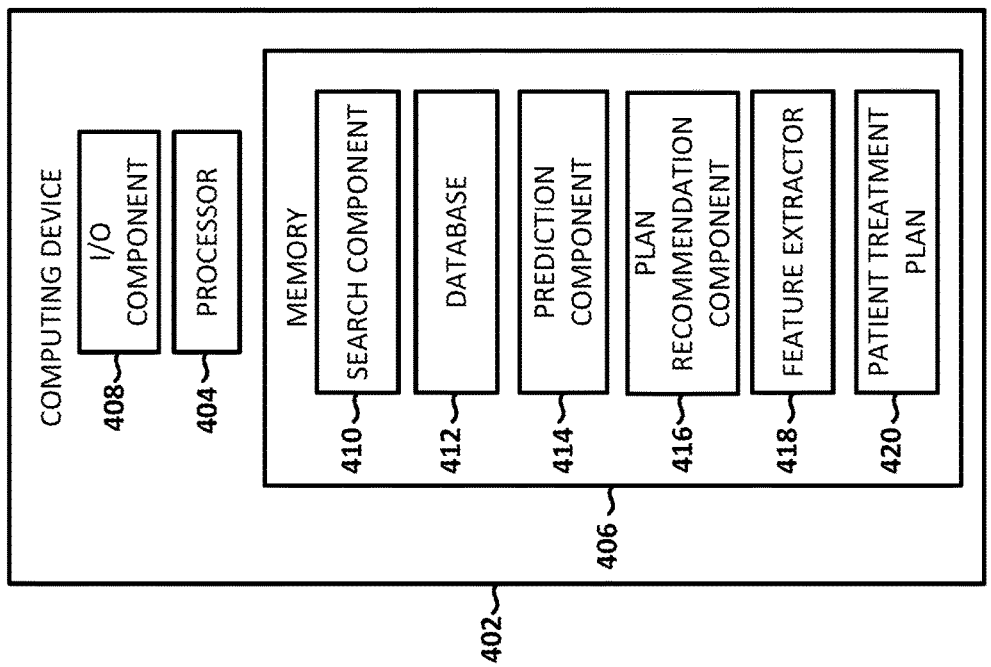

MULTI-OBJECTIVE RADIATION THERAPY SELECTION SYSTEM AND METHOD

CROSS-REFERENCE TO RELATED APPLICATION

This application is a continuation of U.S. patent application Ser. No. 14/310,925, filed on Jun. 20, 2014, now patented, U.S. Pat. No. 9,925,391, which claims the benefit of Provisional Application No. 61/837,754, filed Jun. 21, 2013, and Provisional Application No. 61/877,291, filed Sep. 13, 2013, which are both herein incorporated by reference in their entireties.

TECHNICAL FIELD

This application is generally related to facilitating creation of radiation treatment plans.

BACKGROUND

Providing radiation therapy to patients diagnosed with cancer includes creating a radiation treatment plan. Often, where the cancer is localized in the patient's anatomy, such as in a tumor, the creation of the radiation treatment plan involves participation by medical personnel for solving a difficult geometric problem and/or making judgment calls related to the total radiation dose or total dose received by the tumor and nearby healthy tissue, including organs at risk (OARs). Creating the radiation treatment plan can be a time consuming process that involves multiple medical personnel providing multiple iterations of the treatment plan over many days, which may increase the time from diagnosis of the cancer to treatment of the cancer.

In an example of a conventional process for the diagnosis and treatment of tumors, a diagnostic scan, such as a computed tomography (CT) scan, is taken of the patient to localize a tumor and a biopsy of the tumor is taken to histologically verify that the tumor is malignant. Next, treatment contours of the three dimensional envelope defined by the tumor's shape and the shape of the OARs are drawn up and a treatment prescription is developed by a clinician or an oncologist. The treatment prescription prescribes a total radiation dose to be delivered to the tumor over the course of treatment and a maximum level of radiation to be absorbed by the OARS. Next, the treatment prescription is provided to medical personnel, such as a dosimetrist, and a radiation delivery plan is developed by the medical personnel. The radiation delivery plan includes radiation beam orientations, shapes, and fluences using a given radiation type and delivery method to achieve the radiation levels, including the total dose levels, defined by the treatment prescription. Treatment constraints, including at least the treatment prescription and the radiation delivery plan, are iteratively changed by the medical personnel to meet minimum standards and to satisfy the oncologist. The final iteration of the radiation delivery plan is used to treat the patient.

This process for developing a radiation treatment plan can take many days, especially in cases in which the medical personnel, including the dosimetrist and/or the oncologist, change the treatment constraints over a number of iterative cycles.

SUMMARY

Embodiments of the invention include systems and methods for facilitating creation of patient treatment plans based on parameters from previously planned patient treatments. Embodiments of the invention may facilitate providing medical personnel with treatment information for creating achievable radiation treatment plans, saving hours and days of labor, and reducing the time from diagnosis of the cancer to treatment of the cancer.

According to Example 1, a system for facilitating creation of a patient treatment plan comprises memory that stores computer-executable instructions and at least one processor configured to execute the computer-executable instructions, which, when executed, cause the at least one processor to provide a number of components. In embodiments, the components include a search component configured to identify, based on one or more features associated with patient data, at least one matching plan from a database of previously planned radiation treatments; and a user interface configured to present, to a user, one or more parameters associated with the at least one matching plan.

In Example 2, the system of Example 1, wherein the one or more features associated with patient data include at least one of a physics parameter, a treatment type parameter, a patient image parameter, and a disease parameter.

In Example 3, the system of any of Examples 1 and 2, wherein the one or more features associated with patient data include a patient image parameter and the computer-executable instructions, when executed, cause the at least one processor to further provide a feature extractor configured to extract from a patient image the patient image parameter.

In Example 4, the system of any of Examples 1-3, wherein the one or more features associated with patient data include a patient image parameter extracted from a patient image that comprises an imaging scan of the patient produced by one or more of ionizing energy, acoustic energy, computed tomography, magnetic resonance imaging, positron emission tomography, an x-ray, and fluoroscopy.

In Example 5, the system of any of Examples 1-4, wherein the one or more parameters associated with the at least one matching plan include at least one of a physics parameter, a treatment type parameter, an image parameter, and a disease parameter.

In Example 6, the system of any of Examples 1-5, wherein the computer-executable instructions, when executed, cause the at least one processor to further provide a prediction component configured to determine at least one metric that includes a predictor of a treatment outcome.

In Example 7, the system of any of Examples 1-6, wherein the computer-executable instructions, when executed, cause the at least one processor to further provide a prediction component configured to determine at least one metric that includes a combination of two or more of the parameters associated with the at least one matching plan.

In Example 8, the system of any of Examples 1-7, wherein the computer-executable instructions, when executed, cause the at least one processor to further provide a prediction component configured to determine at least one metric using at least one of a machine learning technique, a pattern matching technique, and a data mining technique.

In Example 9, the system of any of Examples 1-5, wherein the search component is configured to identify a plurality of matching plans from the database of previously planned radiation treatments and the computer-executable instructions, when executed, cause the at least one processor to further provide a prediction component configured to determine at least one metric that is correlated to a treatment dose and to use the at least one metric to facilitate selection of one of the plurality of matching plans.

In Example 10, the system of Example 9, wherein the at least one metric comprises a predictor of a treatment outcome.

In Example 11, the system of any of Examples 9 and 10, wherein the at least one metric comprises a combination of two or more of the parameters associated with the at least one matching plan.

In Example 12, the system of any of Examples 9-11, wherein the prediction component is configured to determine the at least one metric using at least one of a machine learning technique, a pattern matching technique, and a data mining technique.

In Example 13, the system of any of Examples 1-12, wherein the computer-executable instructions, when executed, cause the at least one processor to further provide a plan recommendation component configured to recommend at least one of the previously planned radiation treatments.

In Example 14, the system of Example 13, wherein the plan recommendation component is configured to cause at least one parameter from the at least one matching plan to be inserted automatically into the patient treatment plan.

In Example 15, the system of any of Examples 1-5, wherein the computer-executable instructions, when executed, cause the at least one processor to further provide a prediction component configured to determine at least one metric that is correlated to a treatment dose.

In Example 16, the system of Example 15, wherein the search component is configured to identify a plurality of matching plans from the database of previously planned radiation treatments, and the prediction component is configured to use the at least one metric to facilitate selection of one of the plurality of matching plans.

In Example 17, the system of any of Examples 15 and 16, wherein the at least one metric comprises a predictor of a treatment outcome.

In Example 18, the system of any of Examples 15-17, wherein the at least one metric comprises a combination of two or more of the parameters associated with the at least one matching plan.

In Example 19, the system of any of Examples 15-18, wherein the prediction component is configured to determine the at least one metric using at least one of a machine learning technique, a pattern matching technique, and a data mining technique.

In Example 20, the system of any of Examples 15-19, wherein the computer-executable instructions, when executed, cause the at least one processor to further provide a plan recommendation component configured to recommend at least one of the previously planned radiation treatments.

In Example 21, the system of Example 20, wherein the plan recommendation component is configured to cause at least one parameter from the at least one matching plan to be inserted automatically into the patient treatment plan.

In Example 22, the system of any of Examples 1-5, wherein the computer-executable instructions, when executed, cause the at least one processor to further provide a plan recommendation component configured to recommend at least one of the previously planned radiation treatments.

In Example 23, the system of Example 22, wherein the plan recommendation component is configured to cause at least one parameter from the at least one matching plan to be inserted automatically into the patient treatment plan.

In Example 24, the system of any of Examples 1-5, wherein the computer-executable instructions, when executed, cause the at least one processor to further cause at least one parameter from the at least one matching plan to be inserted automatically into the patient treatment plan.

In Example 25, the system of any of Examples 1-24, wherein the memory and the at least one processor are located remotely with respect to a point of care that uses the system.

In an Example 26, a method for facilitating creation of a patient treatment plan comprises receiving, by a processor, at least one feature associated with patient data; searching, by the processor, a database of previously planned radiation treatments; identifying, by the processor, a plurality of matching plans from the database based on the at least one feature; and determining, by the processor, at least one metric that is correlated to a treatment dose.

In Example 27, the method of Example 26, further comprising presenting, by a user interface, at least one parameter corresponding to the plurality of matching treatment plans.

In Example 28, the method of any of Examples 26 and 27, further comprising inserting, by the processor, into the patient treatment plan at least one parameter corresponding to the plurality of matching treatment plans.

In Example 29, the method of any of Examples 26-28, further comprising extracting the at least one feature from an imaging scan of the patient.

In Example 30, the method of any of Examples 26-29, wherein determining, by the processor, the at least one metric that is correlated to a treatment dose comprises determining the at least one metric using at least one of a machine learning technique, a pattern matching technique, a data mining technique.

In Example 31, the method of any of Examples 26-30, further comprising selecting, by the processor and based on the at least one metric, one of the plurality of matching treatment plans.

In Example 32, the method of Example 31, further comprising presenting, by a display device, at least one parameter corresponding to the selected one of the plurality of matching treatment plans.

In Example 33, the method of any of Examples 31 and 32, further comprising inserting, by the processor, into the patient treatment plan at least one parameter corresponding to the selected one of the plurality of matching treatment plans.

In Example 34, the method of any of Examples 31-33, further comprising extracting the at least one feature from an imaging scan of the patient.

In Example 35, the method of any of Examples 31-34, wherein determining, by the processor, the at least one metric that is correlated to a treatment dose comprises determining the at least one metric using at least one of a machine learning technique, a pattern matching technique, a data mining technique.

In an Example 36, one or more non-transitory computer-readable storage media have computer-executable instructions embodied thereon that, when executed by a processor, cause the processor to instantiate a plurality of computer program components. In embodiments, the plurality of computer program components comprise a search component configured to identify, based on one or more features associated with patient data, a plurality of matching plans from a database of previously planned radiation treatments; a prediction component configured to determine at least one metric that is correlated to a treatment dose and to facilitate selection of one of the plurality of matching plans using the at least one metric; and a user interface configured to present, to a user, one or more parameters associated with the one of the plurality of matching plans.

In Example 37, the media of Example 36, wherein the at least one metric includes at least one of a predictor of a treatment outcome and a combination of two or more of the parameters associated with the one of the plurality of matching plans.

In Example 38, the media of any of Examples 36 and 37, wherein the plurality of computer program components comprises a plan recommendation component configured to cause at least one parameter from the one of the plurality of matching plans to be inserted automatically into a patient treatment plan.

BRIEF DESCRIPTION OF THE DRAWINGS

FIG. 1 is a block diagram illustrating a system for facilitating creation of a patient treatment plan in accordance with embodiments of the present invention;

FIG. 2 is a block diagram illustrating an extraction system for creating a processed database from a medical data database in accordance with embodiments of the present invention;

FIG. 4 is a block diagram illustrating a computing device for implementing aspects of a system for facilitating creation of a treatment plan in accordance with embodiments of the present invention; and FIG. 5 is a flow diagram depicting an illustrative method for facilitating creation of a patient treatment plan in accordance with embodiments of the present invention.

Figure 3:
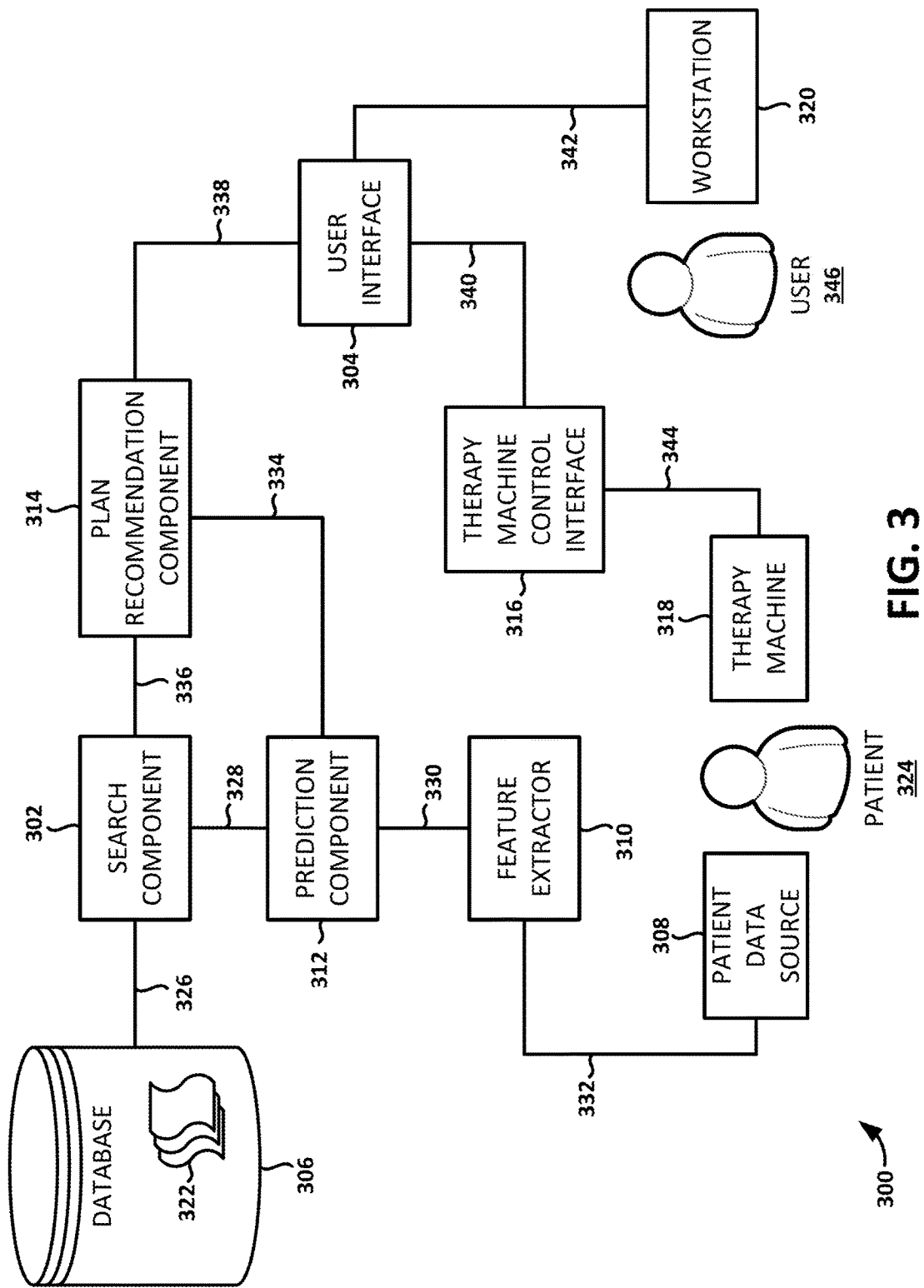
FIG. 3 is a block diagram illustrating another system for facilitating creation of a patient treatment plan in accordance with embodiments of the present invention.

While the present invention is amenable to various modifications and alternative forms, specific embodiments have been shown by way of example in the drawings and are described in detail below. The present invention, however, is not limited to the particular embodiments described. On the contrary, the present invention is intended to cover all modifications, equivalents, and alternatives falling within the ambit of the present invention as defined by the appended claims.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

FIG. 1 is a block diagram illustrating a system 100 for facilitating creation of a patient treatment plan in accordance with embodiments of the invention. The system 100 may be used, for example, to facilitate creation of a radiation treatment plan for a cancer patient. In embodiments, non-transitory computer-readable storage media or memory that stores computer-executable instructions, and at least one processor configured to execute the computer-executable instructions may provide one or more components of the system 100. As shown in FIG. 1, the system 100 includes a search component 102, a user interface 104, and a database 106. The search component 102 is communicatively coupled to the database 106 by communications path 108 and to the user interface 104 by communications path 110. Additionally, in embodiments, the user interface 104 may be communicatively coupled to the database 106.

The communications paths 108 and 110 may include any type of communication path suitable for facilitating unidirectional and/or bidirectional communications between the connected components. For example, the communications paths 108 and 110 may be, or include, wired communications paths, wireless communications paths, and/or a combination thereof. In embodiments, communication path 108 and 110 may be, or include, a network or networks. The network may be, or include, any number of different types of communication networks such as, for example, a bus network, a short messaging service (SMS), a local area network (LAN), a wireless LAN (WLAN), a wide area network (WAN), the Internet, a P2P network, and/or the like. In embodiments, the network may include a combination of multiple networks.

The database 106 may be, or include, one or more tables, one or more relational databases, one or more multi-dimensional data cubes, and/or the like. Further, though illustrated as a single component, the database 106 may, in fact, be a plurality of databases 106 such as, for instance, a database cluster, which may be implemented on a single computing device or distributed between a number of computing devices, memory components, or the like. According to embodiments, the database 106 may include information associated with previously planned radiation treatments such as, for example, previously planned radiation treatments that were approved for use on patients by medical personnel, previously planned radiation treatments that were used on patients by medical personnel, and/or the like. In embodiments, treatment outcomes may be included in the database 106. In embodiments, the database 106 includes a medical data database that includes medical data associated with the previously planned radiation treatments. In embodiments, the database 106 includes a processed database configured to store selected data that have been extracted and, in embodiments, transformed (e.g., using a process for determining one or more characteristics, as described in more detail below), from a medical data database and stored in the processed database.

According to embodiments of the invention, the search component 102 may be any type of search component configured to search the database 106 using one or more features associated with patient data and identifies one or more radiation treatment plans from the database 106 that matches the one or more features associated with the patient data. In embodiments, a radiation treatment plan that matches a feature may refer to, for example, a treatment plan having one or more characteristics (e.g., parameters, features, metrics, aspects, and/or the like) that are identical to, similar to, associated with, correlated with, and/or derivable from the feature (or features), one or more characteristics (e.g., parameters, features, metrics, aspects, and/or the like) of the features, and/or the like. In embodiments, any number of different types of searching techniques and/or algorithms may be utilized to identify matching treatment plans, and may include statistical techniques, pattern-matching techniques, artificial intelligence techniques, and/or the like. In embodiments, for example, the search component 102 may include a search engine, a query module, a database management component, and/or the like. The search component 102 may receive the one or more features associated with the patient data from the user interface 104. That is, for example, a user (e.g., a clinician) may input, via the user interface 104, search criteria including the one or more features associated with the patient data. In embodiments, the search component 102 may receive search criteria from other sources in addition to, or in lieu of, the user interface 104.

The one or more features associated with patient data may include a physics parameter, a treatment type parameter, a patient image parameter, a disease parameter, and/or the like. In embodiments, physics parameters may be, or include, for example, penumbra, aperture, incident angle, beam energy, radiation type, depth of structure, existence of bolus, and/or the like. Treatment type parameters may be, or include, fractionation schedule, treatment margin, number of beams/arcs, interpretation of contours, the clinicians who are part of the team creating the radiation treatment plan, and/or the like. Patient image parameters may be, or include, distance, volume, geometric relationship, importance of structures and surrounding structures, and/or the like. Disease parameters may be, or include, disease stage, prior or post treatment therapy, prior radiation therapy, prior radiation damage to nearby tissue, disease type, disease histology, extent of the disease, prior disease, and/or the like.

According to embodiments, the search component 102 searches the database 106 using at least one of the features, which may include the physics parameters, the treatment type parameters, the patient image parameters, and the disease parameters, and matches the at least one parameter to information (e.g., at least one treatment plan, at least one feature, at least one parameter, and/or the like) from the database 106. For example, by matching the at least one parameter to one or more previously planned radiation treatments, embodiments of the invention may facilitate selection of the closest matching treatments for providing information to medical personnel and/or facilitating creation of a patient treatment plan.

According to embodiments, the user interface 104 may be configured to present, to a user, one or more parameters associated with the radiation treatment plan (or plans) identified by the search component 102. In embodiments, the user interface 104 may provide read and/or write access to the search component 102 and/or the database 106. In embodiments, the user interface 104 may be, include, and/or be configured to interact with a keyboard, a mouse, a visual display, and/or the like. In embodiments, for example, the user interface 104 may be, or include, text output, print-outs, and/or the like, and/or a graphical user interface (GUI) implemented in hardware, firmware, software, or a combination thereof.

The one or more parameters associated with the treatment plan or plans identified by the search component 102 may include a physics parameter, a treatment type parameter, an image parameter, a disease parameter, and/or the like. In embodiments, physics parameters may be, or include, penumbra, aperture, incident angle, beam energy, radiation type, depth of structure, existence of bolus, and/or the like. Treatment type parameters may be, or include, fractionation schedule, treatment margin, number of beams/arcs, interpretation of contours, the clinicians who are part of the team creating the radiation treatment plan, and/or the like. Patient image parameters related to the patient's anatomy may be, or include, distance, volume, geometric relationship, importance of structures and surrounding structures, and/or the like. Disease parameters may be, or include, disease stage, prior or post treatment therapy, prior radiation therapy, prior radiation damage to nearby tissue, disease type, disease histology, extent of the disease, prior disease, and/or the like.

The illustrative system 100 shown in FIG. 1 is not intended to suggest any limitation as to the scope of use or functionality of embodiments of the present invention. Neither should the illustrative system 100 be interpreted as having any dependency or requirement related to any single component or combination of components illustrated therein. Additionally, any one or more of the components depicted in FIG. 1 may be, in embodiments, integrated with various ones of the other components depicted therein (and/or components not illustrated), all of which are considered to be within the ambit of the present invention. For example, the user interface 104 may be integrated with the search component 102.

FIG. 2 is a block diagram illustrating an extraction system 200 for creating a processed database 202 from a medical data database 204 in accordance with embodiments of the invention. In embodiments, the processed database 202 and/or the medical database 204 may be, include, be identical to, and/or be similar to database 106 shown in FIG. 1. The processed database 202 and/or the medical database 204 may be, or include, one or more tables, one or more relational databases, one or more multi-dimensional data cubes, and/or the like. Further, though each is illustrated as a single component, the processed database 202 and/or the medical database 204 may, in fact, be a plurality of databases 202, 204 such as, for instance, a database cluster, which may be implemented on a single computing device or distributed between a number of computing devices, memory components, or the like.

According to embodiments, the extraction system 200 includes a database extractor 206 configured to create the processed database 202. The database extractor 206 may be configured to extract information from the medical data database 204 and stores the extracted information in the processed database 202. In embodiments, the database extractor 206 may be configured to process the extracted information before saving it in the processed database 202. For example, the database extractor 206 may be configured to extract certain parameters, compute additional parameters and/or metrics based on the extracted parameters, and store the computed parameters and/or metrics in the processed database 202. In embodiments, non-transitory computer-readable storage media or memory that stores computer-executable instructions, and at least one processor configured to execute the computer-executable instructions may provide the database extractor 206, the medical database 204, and/or the processed database 202.

Additionally, as shown in FIG. 2, the database extractor 206 may be communicatively coupled to the medical data database 204 by communications path 208 and to the processed database 202 by communications path 210. The communications paths 208 and 210 may include any type of communication path suitable for facilitating unidirectional and/or bidirectional communications between the connected components. For example, the communications paths 208 and 210 may be, or include, wired communications paths, wireless communications paths, and/or a combination thereof. In embodiments, communication path 208 and 210 may be, or include, a network or networks. The network may be, or include, any number of different types of communication networks such as, for example, a bus network, a short messaging service (SMS), a local area network (LAN), a wireless LAN (WLAN), a wide area network (WAN), the Internet, a P2P network, and/or the like. In embodiments, the network may include a combination of multiple networks.

The illustrative system 200 shown in FIG. 2 is not intended to suggest any limitation as to the scope of use or functionality of embodiments of the present invention. Neither should the illustrative system 200 be interpreted as having any dependency or requirement related to any single component or combination of components illustrated therein. Additionally, any one or more of the components depicted in FIG. 2 may be, in embodiments, integrated with various ones of the other components depicted therein (and/or components not illustrated), all of which are considered to be within the ambit of the present invention. For example, the processed database 202 may be integrated with the medical data database 204.

FIG. 3 is a block diagram illustrating another system 300 for facilitating creation of a patient treatment plan in accordance with embodiments of the invention. The system 300 may be used, for example, to facilitate creation of a radiation treatment plan for a cancer patient. In embodiments, non-transitory computer-readable storage media or memory that stores computer-executable instructions, and at least one processor configured to execute the computer-executable instructions may be used to provide one or more components of the system 300.

As shown in FIG. 3, the system 300 includes a search component 302, a user interface 304, and a database 306. The search component 302 may be, include, be identical to, and/or be similar to the search component 102 (shown in FIG. 1); the user interface 304 may be, include, be identical to, and/or be similar to the user interface 104 (shown in FIG. 1); and the database 306 may be, include, be identical to, and/or be similar to the database 106 (shown in FIG. 1), the processed database 202 (shown in FIG. 2), and/or the medical database 204 (shown in FIG. 2). As is further shown in FIG. 3, the system 300 includes a patient data source 308, a feature extractor 310, a prediction component 312, a plan recommendation component 314, a therapy machine control interface 316, a therapy machine 318, and a workstation 320.

The search component 302 may be configured to search the database 306 using one or more features associated with patient data (e.g., that is obtained by the patient data source 308) and identify one or more treatment plans 322 from the database 306 that match the one or more features associated with the patient data. According to embodiments, patient data may include information about a patient 324 such as, for example, one or more physics parameters, treatment type parameters, patient image parameters, disease parameters, and/or the like. In embodiments, the search component 302 searches the database 306 and identifies a number of treatment plans 322 in the database 306 that match the one or more features associated with the patient data. According to embodiments, the search component 302 may receive one or more features associated with the patient data via the patient data source 308, the user interface 304, and/or the like. Additionally, in embodiments, the search component 302 may be configured to be modified (e.g., enhanced) during use. That is, for example, the search component 302 may include aspects of artificial intelligence (e.g., one or more classifiers, neural networks, and/or other machine-learning techniques) that enable the search component to be dynamically updated based on explicit and/or inferred user preferences, search result trends, and/or the like.

As shown in FIG. 3, the search component 302 is communicatively coupled to the database 306 by communications path 326 and to the prediction component 312 by communications path 328. The prediction component 312 is communicatively coupled to the feature extractor 310 by communications path 330 and the feature extractor 310 is communicatively coupled to the patient data source 308 by communications path 332. The plan recommendation component 314 is communicatively coupled to the prediction component 312 by communications path 334, to the search component 302 by communications path 336, and to the user interface 304 by communications path 338. The user interface 304 is communicatively coupled to the therapy machine control interface 316 by communications path 340 and to the workstation by communications path 342. The therapy machine control interface 316 is communicatively coupled to the therapy machine 318 by communications path 344.

The communications paths 326-344 may include any type of communication path suitable for facilitating unidirectional and/or bidirectional communications between the connected components. For example, the communications paths 326-344 may be, or include, wired communications paths, wireless communications paths, and/or a combination thereof. In embodiments, communication paths 326-344 may be, or include, a network or networks. The network may be, or include, any number of different types of communication networks such as, for example, a bus network, a short messaging service (SMS), a local area network (LAN), a wireless LAN (WLAN), a wide area network (WAN), the Internet, a P2P network, and/or the like. In embodiments, the network may include a combination of multiple networks.

According to embodiments, the feature extractor 310 may be configured to extract information, including patient image parameters that include geometrical and compositional features related to the anatomy of the patient 324, from patient data obtained by the patient data source 308. In embodiments, the feature extractor 310 may provide the extracted information to the search component 302 (e.g., via a communications path not illustrated in FIG. 3), through the prediction component 312, and/or the like. The search component 302 may receive one or more features associated with patient data such as, for example, patient image parameters, and may use the received features to search the database 306. In embodiments, patient imaging parameters may include distance, volume, geometric relationship, importance of structures and surrounding structures in the patient 324, and/or the like. In embodiments, features (e.g., patient imaging parameters) may be provided to the search component 302 via the user interface 304.

In embodiments, the patient data source 308 may be, or include, a patient imaging system configured to obtain patient images, from which patient image parameters may be extracted. In such embodiments, the imaging system may obtain an image of the patient 324 and stores the image in a database (e.g., database 306). The feature extractor 310 may be configured to extract patient image parameters from the image of the patient 324 and provide the extracted patient image parameters to the prediction component 312 and/or the search component 302. According to embodiments, patient imaging systems may use ionizing energy to produce an image of the patient 324. In embodiments, patient imaging systems may use acoustic energy to produce an image of the patient 324. In embodiments, patient imaging systems may use any number and/or combination of these and/or other technologies such as, for example, computed tomography, magnetic resonance imaging, positron emission tomography, x-ray, fluoroscopy, and/or the like. In embodiments, the patient data source 308 may include medical data about the patient such as, for example, current and historical data which may include patient history, and/or the like, and which may be stored one any number of databases. In embodiments, the patient data source 308 may include a source of demographic data, financial data, and/or any other type of data related to the patient. The patient data source 308 may include any number of different types of sources such as, for example, internal databases, memory devices, networks, external servers, third party vendors, a user interface, a machine interface (e.g., an interface to a patient monitoring device), and/or the like.

According to embodiments, the prediction component 312 may determine at least one metric related to patient treatment and, where the search component 302 identifies a number of treatment plans 322, the prediction component 312 may facilitate selection of one or more of the identified treatment plans 322 using the at least one metric. In embodiments, metrics may be correlated to a radiation treatment dose and/or may include a predictor of a treatment outcome.

The prediction component 312 may determine the at least one metric using information in the database 306, patient data, and/or the like. In embodiments, the prediction component 312 may be configured to determine the at least one metric using any number of different types of techniques, algorithms, and/or the like such as, for example, machine learning techniques, pattern matching techniques, data mining techniques, ensemble techniques, and/or the like. In embodiments, for example, the prediction component 312 may be configured to determine the at least one metric using a neural net, a support vector machine, and/or the like. In embodiments, the at least one metric may include a combination of two or more of the parameters associated with the one or more treatment plans 322 (e.g., treatment plans identified by the search component 302). In embodiments, the prediction component 312 may receive treatment parameters from the user interface 304. In embodiments, the prediction component 312 may receive one or more patient image parameters from the feature extractor 310.

According to embodiments, the plan recommendation component 314 may be configured to recommend at least one of the previously planned radiation treatments (e.g., one or more identified treatment plans 322) to a user. In embodiments, the plan recommendation component 314 may be configured to cause one or more parameters to be inserted (e.g., automatically, in response to a user input, etc.) into a patient treatment plan being created using aspects of embodiments of the system 300.

The user interface 304 may be configured to present one or more parameters, to a user 346, from a treatment plan or plans identified by the search component 302, including, for example, a treatment plan selected using a metric determined by the prediction component 312. In embodiments, the user interface 304 may provide read and/or write access to a patient treatment plan being created for the patient 324. That is, for example, according to embodiments, a user 346, via the user interface 304, may view matching treatment plans identified by the search component 302; view and/or edit a patient treatment plan being created for the patient 324; interact with (e.g., obtain data from, monitor, control, and/or the like) the therapy machine 318; and/or the like. For example, a final radiation treatment plan created for the patient 324 may be provided for configuring the therapy machine 318 via the therapy machine control interface 316. In embodiments, user 346 may interact with the therapy machine control interface 316 via the user interface 304, via another user interface (not illustrated), and/or the like. In embodiments, the therapy machine control interface 316 facilitates interaction with, and/or control of, the therapy machine 318, which is configured to deliver radiation therapy to the patient 324.

In embodiments, the user interface 304 may provide read and/or write access to any one or more components depicted in FIG. 3. In embodiments, the user interface 304 may be, include, and/or be configured to interact with a keyboard, a mouse, a visual display, and/or the like. In embodiments, for example, the user interface 304 may be, or include, a graphical user interface (GUI) implemented in hardware, firmware, software, or a combination thereof.

The illustrative system 300 shown in FIG. 3 is not intended to suggest any limitation as to the scope of use or functionality of embodiments of the present invention. Neither should the illustrative system 300 be interpreted as having any dependency or requirement related to any single component or combination of components illustrated therein. Additionally, any one or more of the components depicted in FIG. 3 may be, in embodiments, integrated with various ones of the other components depicted therein (and/or components not illustrated), all of which are considered to be within the ambit of the present invention. For example, the prediction component 312 may be integrated with the search component 302, the plan recommendation component, and/or the like. Additionally, in embodiments, the user interface 304 may be integrated with the therapy machine control interface 316, and/or hosted by the workstation 320, which, in embodiments, may be integrated with, include, or be included within the therapy machine 318.

According to embodiments, any one or more components of embodiments of the systems described herein (e.g., the system 100, the system 200, the system 300, and/or the like) may be implemented on a computing device 402 that includes a processor 404, a memory 406, and an input/output (I/O) component 408. Various aspects and/or components of embodiments of the invention may be implemented on a single computing device 402, on multiple computing devices 402, in multiple server instances (e.g., as a server cluster), instantiated within multiple virtual machines, and/or the like. In embodiments, the processor 404 executes various program components stored in the memory 406, which may facilitate creation of a patient treatment plan. In embodiments, the processor 404 may be, or include, one processor or multiple processors. In embodiments, the I/O component 408 may be, or include, one or more devices and/or user interfaces (e.g., the user interface 104, the user interface 304, and/or the like), and may be implemented in hardware, firmware, software, or a combination thereof Examples of I/O devices include, for example, a monitor, a keyboard, a printer, a disk drive, a universal serial bus (USB) port, a speaker, pointer device, a trackball, a button, a switch, a touch screen, and the like.

The computing device 402 may include any type of computing device suitable for implementing embodiments of the invention. Examples of computing devices include specialized computing devices or general-purpose computing devices such "workstations," "servers," "laptops," "desktops," "tablet computers," "hand-held devices," and the like, all of which are contemplated within the scope of the figures with reference to various components of the embodiments of the invention. In embodiments, a computing device includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in embodiments, the computing device may include a number of processors, a number of memory components, a number of I/O ports, a number of I/O components, and/or a number of power supplies. Additionally any number of these components, or combinations thereof, may be distributed and/or duplicated across a number of computing devices, which may be distributed geographically.

In embodiments, the memory 406 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; or any other medium that can be used to store information and can be accessed by a computing device such as, for example, quantum state memory, and the like. In embodiments, the memory 406 stores computer-executable instructions for causing the processor 404 to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed, manipulated, edited, presented, and/or stored, by one or more processors associated with a computing device. Examples of such program components include a search component 410 (which may be, include, be identical to, and/or be similar to the search component 102 depicted in FIG. 1 and/or the search component 302 depicted in FIG. 3); a database 412 (which may be, include, be identical to, and/or be similar to the database 106 depicted in FIG. 1, the processed database 202 depicted in FIG. 2, the medical database 204 depicted in FIG. 2, and/or the database 306 depicted in FIG. 3); a prediction component 414 (which may be, include, be identical to, and/or be similar to the prediction component 312 depicted in FIG. 3); a plan recommendation component 416 (which may be, include, be identical to, and/or be similar to the plan recommendation component 314 depicted in FIG. 3); a feature extractor 418 (which may be, include, be identical to, and/or be similar to the feature extractor 310 depicted in FIG. 3); a patient treatment plan 420 (which may be, include, be identical to, and/or be similar to the patient treatment plans 322 depicted in FIG. 3); and/or the like. Some or all of the functionality contemplated herein may be implemented in hardware, firmware, software, and/or the like.

The illustrative computing device 402 shown in FIG. 4 is not intended to suggest any limitation as to the scope of use or functionality of embodiments of the present invention. Neither should the illustrative computing device 402 be interpreted as having any dependency or requirement related to any single component or combination of components illustrated therein. Additionally, any one or more of the components depicted in FIG. 4 may be, in embodiments, integrated with various ones of the other components depicted therein (and/or components not illustrated), all of which are considered to be within the ambit of the present invention. For example, in embodiments, the processor 404 and the memory 406 may be located remotely with respect to a point of care (e.g., the therapy machine 318 depicted in FIG. 3) that uses the system for creating the radiation treatment plan.

FIG. 5 is a flow diagram depicting an illustrative method 500 for facilitating creation of a patient treatment plan in accordance with embodiments of the invention. In embodiments, aspects of embodiments of the method 500 may be performed, for example, by one or more components of embodiments of the system 100 depicted in FIG. 1, the system 200 depicted in FIG. 2, the system 300 depicted in FIG. 3, and/or the computing device 402 depicted in FIG. 4.

The illustrative method 500 includes receiving at least one feature associated with patient data (block 502). In embodiments, the at least one feature associated with patient data may be provided through a user interface, a patient data source (e.g., the patient data source 308 depicted in FIG. 3), and/or the like. The at least one feature associated with patient data may include, for example, at least one of a physics parameter, a treatment type parameter, a patient image parameter, a disease parameter, and/or the like. In embodiments, to provide at least one patient image parameter, an imaging system may be configured to obtain an image of the patient from which a feature extractor may extract the at least one patient image parameter.

In embodiments, a physics parameter may include a penumbra, aperture, incident angle, beam energy, radiation type, depth of structure, existence of bolus, and/or the like. A treatment type parameter may include fractionation schedule, treatment margin, number of beams/arcs, interpretation of contours, the clinicians who are part of the team creating the radiation treatment plan, and/or the like. A patient image parameter may include distance, volume, geometric relationship, importance of structures and surrounding structures, and/or the like. Additionally, in embodiments, a disease parameter may include disease stage, prior or post treatment therapy, prior radiation therapy, prior radiation damage to nearby tissue, disease type, disease histology, extent of the disease, prior disease, and/or the like.

As shown in FIG. 5, embodiments of the method 500 include searching a database (e.g., the database 412 depicted in FIG. 4) of previously planned radiation treatments (block 504). In embodiments, for example, a search component (e.g., the search component 410 depicted in FIG. 4) searches the database using the at least one feature associated with patient data. In embodiments, the database includes previously planned radiation treatments that have been approved for use on patients by medical personnel. In embodiments, the database includes previously planned radiation treatments that have been used on patients by medical personnel, such that results and/or outcomes may be included in the database.

Embodiments of the method 500 further include identifying at least one matching treatment plan based on the at least one feature associated with patient data (block 506). For example, in embodiments, the search component may identify the at least one matching treatment plan from the database, which matches the at least one feature associated with patient data. In embodiments, the processor searches the database and identifies a number of matching treatment plans in the database that match the at least one feature associated with patient data.

Embodiments of the method 500 further include determining at least one metric that is correlated to a treatment dose (block 508). In embodiments, for example, a prediction component (e.g., the prediction component 414 depicted in FIG. 4) may be configured to determine the at least one metric using the database of previously planned treatments. In embodiments, the prediction component may determine the at least one metric using a machine learning technique, a pattern matching technique, a data mining technique, an ensemble technique, and/or the like. The at least one metric may be used, for example, to select one or more matching treatment plans from a number of matching treatment plans identified by the search component.

In embodiments, the method 500 includes presenting, by a user interface, at least one parameter corresponding to the at least one matching treatment plan or plans identified by the search component (block 510). In this manner, embodiments of the invention may facilitate providing a user the opportunity to review the parameter(s) for inclusion in a patient treatment plan that is being created by the user. In embodiments, a plan recommendation component (e.g., the plan recommendation component 416 depicted in FIG. 4) may be used to insert into a patient treatment plan at least one parameter corresponding to the at least one matching treatment plan.

While embodiments of the present invention are described with specificity, the description itself is not intended to limit the scope of this patent. Thus, the inventors have contemplated that the claimed invention might also be embodied in other ways, to include different steps or features, or combinations of steps or features similar to the ones described in this document, in conjunction with other technologies.

The following is claimed:

1. A system for facilitating creation of a new radiation treatment plan, the system comprising:
    a database of previously planned radiation treatment plans of other patients for radiation treatment;
    memory that stores computer-executable instructions; and
    at least one processor configured to execute the computer-executable instructions, which, when executed, cause the at least one processor to provide:
        a feature extractor configured to receive one or more features associated with patient data of a patient who is to receive radiation treatment for creation of the new radiation treatment plan for the patient;
        a prediction component configured to predict, based on the one or more features associated with patient data, at least one metric comprising a predictor of a treatment outcome, wherein the prediction component has learned using previously planned radiation treatment plans to predict the at least one metric based on features extracted from patient data of patients associated with previously planned radiation treatment plans;
        a search component configured to search the database and identify, based on the at least one predicted metric, at least one radiation treatment plan from the database of previously planned radiation treatment plans, the at least one radiation treatment plan identified as having a match to the at least one predicted metric; and
        a user interface configured to present, to a user, the at least one identified radiation treatment plan or one or more parameters associated with the at least one identified radiation treatment plan as a recommendation for creation of the new radiation treatment plan.

2. The system of claim 1, wherein the one or more features associated with patient data include at least one of a physics parameter, a treatment type parameter, a patient image parameter, and a disease parameter.

3. The system of claim 1, wherein the one or more features associated with patient data include a patient image parameter, and wherein the feature extractor is further configured to extract from a patient image the patient image parameter.

4. The system of claim 1, wherein the one or more parameters associated with the at least one identified radiation treatment plan include at least one of a physics parameter, a treatment type parameter, an image parameter, and a disease parameter.

5. The system of claim 1, wherein the prediction component is further configured to determine the at least one metric using at least one of a machine learning technique, a pattern matching technique, and a data mining technique.

6. The system of claim 1, wherein the computer-executable instructions, when executed, cause the at least one processor to further cause at least one parameter from the at least one identified radiation treatment plan to be inserted automatically into the new radiation treatment plan.

7. The system of claim 1, wherein the memory and the at least one processor are located remotely with respect to a point of care that uses the system.

8. The system of claim 1, wherein having the match comprises having one or more parameters that are identical to, similar to, associated with, correlated with, or derivable from the at least one predicted metric.

9. The system of claim 1, wherein the search component is further configured to dynamically update based on at least one of the following: explicit user preferences, inferred user preferences, and search result trends.

10. The system of claim 9, wherein the search component is configured to dynamically update using one or more classifiers, neural networks, and machine learning techniques.

11. A method for facilitating creation of a new radiation treatment plan, the method comprising:
    receiving, by a processor, one or more features associated with patient data of a patient who is to receive radiation treatment for creation of the new radiation treatment plan for the patient;
    providing the one or more features to a prediction component to predict at least one metric comprising a predictor of a treatment outcome, wherein the prediction component has learned using previously planned radiation treatment plans to predict the at least one metric based on features extracted from patient data of patients associated with previously planned radiation treatment plans;
    receiving, from the prediction component, a prediction of the at least one metric for the patient based on the one or more features associated with patient data of the patient who is to receive radiation treatment;
    searching, by a search component, a database of previously planned radiation treatment plans of other patients for radiation treatment plans having a match to the at least one predicted metric;
    identifying, by the processor, at least one radiation treatment plan from the database having the match to the at least one predicted metric; and
    providing for display to a user in a user interface the at least one identified radiation treatment plan or one or more parameters from the at least one identified radiation treatment plan as a recommendation for creation of the new radiation treatment plan.

12. The method of claim 11, further comprising:
    extracting the one or more features from an imaging scan of the patient.

13. The method of claim 11, wherein predicting, by the processor, the at least one predicted metric comprises using at least one of a machine learning technique, a pattern matching technique, a data mining technique.

14. The method of claim 11, further comprising:
    receiving, by the user interface, a selection of one of the at least one identified radiation treatment plan.

15. The method of claim 14, further comprising:
    inserting, by the processor, into the new radiation treatment plan at least one parameter corresponding to the selected one of the at least one identified radiation treatment plan.

16. The method of claim 11, further comprising:
    updating the search component based on at least one of the following: explicit user preferences, inferred user preferences, and search result trends.

17. A computer program product comprising a non-transitory computer-readable storage medium containing computer program code for:
- receiving, by a processor, one or more features associated with patient data of a patient who is to receive radiation treatment for creation of the new radiation treatment plan for the patient;
- providing the one or more features to a prediction component to predict at least one metric comprising a predictor of a treatment outcome, wherein the prediction component has learned using previously planned radiation treatment plans to predict the at least one metric based on features extracted from patient data of patients associated with previously planned radiation treatment plans;
- receiving, from the prediction component, a prediction of the at least one metric for the patient based on the one or more features associated with patient data of the patient who is to receive radiation treatment;
- searching, by a search component, a database of previously planned radiation treatment plans of other patients for radiation treatment plans having a match to the at least one predicted metric;
- identifying, by the processor, at least one radiation treatment plan from the database having the match to the at least one predicted metric; and
- providing for display to a user in a user interface the at least one identified radiation treatment plan or one or more parameters from the at least one identified radiation treatment plan as a recommendation for creation of the new radiation treatment plan.

18. The computer program product of claim 17, further comprising computer program code for:
- extracting the one or more features from an imaging scan of the patient.

19. The computer program product of claim 17, further comprising computer program code for:
- receiving, by the user interface, a selection of one of the at least one identified radiation treatment plan.

20. The computer program product of claim 19, further comprising computer program code for:
- inserting, by the processor, into the new radiation treatment plan at least one parameter corresponding to the selected one of the at least one identified radiation treatment plan.

21. The computer program product of claim 17, further comprising computer program code for:
- updating the search component based on at least one of the following: explicit user preferences, inferred user preferences, and search result trends.

* * * * *